(12) United States Patent
Houser (10) Patent No.: US 7,488,300 B2
(45) Date of Patent: *Feb. 10, 2009

(54) BICENTRIC HINGE FOR USE IN A BRACE

(75) Inventor: Guy M. Houser, Bainbridge Island, WA (US)

(73) Assignee: Thusane, Levallois Perret (FR)

( * ) Notice: Subject to any disclaimer, the term of this patent is extended or adjusted under 35 U.S.C. 154(b) by 320 days.

This patent is subject to a terminal disclaimer.

(21) Appl. No.: 11/051,198

(22) Filed: Feb. 3, 2005

(65) Prior Publication Data

US 2005/0192522 A1 Sep. 1, 2005

Related U.S. Application Data

(63) Continuation-in-part of application No. 10/077,469, filed on Feb. 15, 2002, now Pat. No. 6,969,363.

(60) Provisional application No. 60/542,257, filed on Feb. 5, 2004.

(51) Int. Cl.
*A61F 5/00* (2006.01)
*A47C 17/04* (2006.01)
*E05D 11/10* (2006.01)
*E05D 7/00* (2006.01)

(52) U.S. Cl. .................. 602/16; 602/26; 5/44.1; 5/47; 16/325; 16/326; 16/327; 16/354; 16/357

(58) Field of Classification Search .............. 602/16, 602/26, 23; 128/882; 5/44.1, 47; 16/325–327, 16/354, 357
See application file for complete search history.

(56) References Cited

U.S. PATENT DOCUMENTS 2,573,596 A 10/1951 Young (Continued)

FOREIGN PATENT DOCUMENTS

EP 0641551 3/1995

(Continued)

OTHER PUBLICATIONS

Supplementary European Search Report, European Patent Office, Oct. 19, 2007, Patent No. PCT/US2005003351.

(Continued)

*Primary Examiner*—Patricia Bianco
*Assistant Examiner*—Tarla Patel
(74) *Attorney, Agent, or Firm*—Perkins Coie LLP (57) ABSTRACT

Bicentric hinges for use in braces and methods for operating knee braces and other types of braces are disclosed herein. In one embodiment, a hinge includes a plate, first and second members pivotally coupled to the plate, and a rocker coupled to the plate. The first member is pivotable about a first axis of rotation, and the second member is pivotable about a second axis of rotation spaced apart from the first axis of rotation. The second member is not directly engaged with the first member, and the first member may not be connected to a return mechanism that urges the first member to pivot about the first axis of rotation. The first member has a first recess, and the second member has a second recess. The rocker includes a head at least partially receivable in the first recess and/or the second recess to restrict rotation of one of the first and second members until the other has rotated.

35 Claims, 10 Drawing Sheets

U.S. PATENT DOCUMENTS

| | | | |
|---|---|---|---|
| 2,573,866 | A | 11/1951 | Murphy |
| 3,528,412 | A | 9/1970 | McDavid |
| 3,799,158 | A | 3/1974 | Gardner |
| 4,323,059 | A | 4/1982 | Rambert et al. |
| 4,337,764 | A | 7/1982 | Lerman |
| 4,407,276 | A | 10/1983 | Bledsoe |
| 4,489,718 | A | 12/1984 | Martin |
| 4,493,316 | A | 1/1985 | Reed et al. |
| 4,502,472 | A | 3/1985 | Pansiera |
| 4,520,802 | A | 6/1985 | Mercer et al. |
| 4,599,998 | A | 7/1986 | Castillo |
| 4,620,532 | A | 11/1986 | Houswerth |
| 4,633,867 | A | 1/1987 | Kausek et al. |
| 4,697,583 | A | 10/1987 | Mason et al. |
| 4,802,467 | A | 2/1989 | Pansiera |
| 4,865,024 | A | 9/1989 | Hensley et al. |
| 4,881,299 | A | 11/1989 | Young et al. |
| 4,886,054 | A | 12/1989 | Castillo et al. |
| 4,928,676 | A | 5/1990 | Pansiera |
| 4,938,207 | A | 7/1990 | Vargo |
| 4,961,416 | A | 10/1990 | Moore et al. |
| 4,986,264 | A | 1/1991 | Miller |
| 5,000,170 | A | 3/1991 | Young et al. |
| 5,018,514 | A | 5/1991 | Grood et al. |
| 5,038,765 | A | 8/1991 | Young et al. |
| 5,039,247 | A | 8/1991 | Young et al. |
| 5,060,640 | A | 10/1991 | Rasmusson |
| 5,230,697 | A | 7/1993 | Castillo et al. |
| 5,259,832 | A | 11/1993 | Townsend et al. |
| 5,288,287 | A | 2/1994 | Castillo et al. |
| 5,356,370 | A | 10/1994 | Fleming |
| 5,399,154 | A | 3/1995 | Kipnis et al. |
| 5,419,754 | A | 5/1995 | Hutchins |
| 5,437,611 | A | 8/1995 | Stern |
| 5,443,444 | A | 8/1995 | Pruyssers |
| 5,460,599 | A | 10/1995 | Davis et al. |
| 5,462,517 | A | 10/1995 | Mann |
| 5,472,412 | A | 12/1995 | Knoth |
| 5,507,719 | A | 4/1996 | Freeman |
| 5,586,970 | A | 12/1996 | Morris et al. |
| 5,643,185 | A | 7/1997 | Watson et al. |
| 5,658,241 | A | 8/1997 | Deharde et al. |
| 5,662,596 | A | 9/1997 | Young |
| 5,749,840 | A | 5/1998 | Mitchell et al. |
| 5,772,618 | A | 6/1998 | Mason et al. |
| 5,776,086 | A | 7/1998 | Pansiera |
| 5,782,785 | A | 7/1998 | Herzberg |
| 5,792,084 | A | 8/1998 | Wilson et al. |
| 5,885,235 | A | 3/1999 | Opahle et al. |
| 5,891,061 | A | 4/1999 | Kaiser |
| 6,074,355 | A | 6/2000 | Bartlett |
| RE37,297 | E | 7/2001 | Smith, III |
| 6,314,612 | B1 | 11/2001 | Rennecke et al. |
| 6,387,066 | B1 | 5/2002 | Whiteside |
| 6,390,998 | B1 | 5/2002 | Doyle |
| 6,402,711 | B1 | 6/2002 | Nauert |
| 6,402,713 | B1 | 6/2002 | Doyle |
| 6,413,232 | B1 | 7/2002 | Townsend et al. |
| 6,527,733 | B1 | 3/2003 | Ceriani et al. |
| 6,540,707 | B1 | 4/2003 | Stark |
| 6,540,709 | B1 | 4/2003 | Smits |
| 6,666,837 | B2 | 12/2003 | Weihermuller |
| 6,740,054 | B2 | 5/2004 | Stearns |
| 6,746,413 | B2 | 6/2004 | Reinecke et al. |
| 6,752,775 | B2 | 6/2004 | Seligman et al. |
| 6,875,187 | B2 | 4/2005 | Castillo |
| 6,878,126 | B2 | 4/2005 | Nelson et al. |
| 6,969,363 | B2 * | 11/2005 | Houser .................. 602/16 |
| 2003/0153853 | A1 | 8/2003 | Houser |

FOREIGN PATENT DOCUMENTS

| | | |
|---|---|---|
| EP | 0684026 | 11/1995 |
| EP | 1088534 | 4/2001 |
| EP | 01/66049 | 9/2001 |
| WO | WO92/03110 | 3/1992 |
| WO | WO99/20212 | 4/1999 |
| WO | WO01/66049 | 9/2001 |
| WO | WO02/02035 | 1/2002 |
| WO | WO-0234174 | 5/2002 |

OTHER PUBLICATIONS

Comfy Splints, Elbow and Knee Splints. Online. Internet. May 13, 2002. Available http://www.comfysints.com/elbow-knee.htm (2 pgs).

Dj Orthopedics, Inc., "TROM," Online. Internet. May 13, 2002. Available http://www.donjoy.com/products/feattrom.html (1 pg).

EBI A Biomet Company, "The Edge PCL Opposition Knee Brace," Online. Internet. May 13, 2002. Available http://www.ebimedical.com/products/sportsmed/knee/opposition.html (1 pg).

Generation II USA Inc., "Ligament Braces Extreme Select," Online. Internet. May. 13, 2002. Available http://www.gen2.com/LigBrace/ExtremeSelect.asp?page=pysician (1 pg).

Generation II USA Inc., "OA Braces Unloader Bi-ComPF," Online. Internet. May 13, 2002. Available http://www.gen2.com/Bi-Com/Bi-com.asp?page=physician (2 pgs).

Generation II USA Inc., "PS-1 Patella Stabilizer," Online. Internet. May 13, 2002. Available http://www.gen2.com/PS-1/PS-1.asp?page=pysician (2 pgs).

Innovation Sports—Medical Experts, "ACL Cable System," Online. Internet. May 13, 2002. Available http://www.isports.com/medi.htm (1 pg).

Innovation Sports, "XCL" Online. Internet. May 13, 2002. Available http://www.isports.com/xcl.html (2 pgs).

International Search Report and Written Opinion of PCT Application No. US04/21094, dated Nov. 22, 2004.

Knapp Hinged Knee Orthosis. Online. Internet. May 13, 2002. Available http://www.hely-weber.com/knapphinged.htm (2 pgs).

* cited by examiner

BICENTRIC HINGE FOR USE IN A BRACE

CROSS-REFERENCE TO RELATED APPLICATIONS

This application claims the benefit of U.S. Provisional Patent Application No. 60/542,257, filed Feb. 5, 2004, and is a continuation-in-part of U.S. patent application Ser. No. 10/077,469, entitled "BICENTRIC HINGE FOR USE IN A BRACE," filed Feb. 15, 2002, each of which is hereby incorporated by reference in its entirety.

TECHNICAL FIELD

The present invention relates to bicentric hinges for use in braces.

BACKGROUND

Knee braces are widely used to stabilize and protect the knee joint. For example, knee braces are often used to prevent damage to the anterior cruciate ligament, posterior cruciate ligament, medial collateral ligament, lateral collateral ligament and/or meniscus in a knee joint. Knee braces are particularly useful to protect the knee joint during vigorous athletic activities such as running, basketball, football and skiing, and they are also used to stabilize the knee joint during recovery or rehabilitation from surgery or an injury.

A knee brace typically includes an upper frame, a lower frame, and a hinge connecting the upper frame to the lower frame. The upper frame often has straps that wrap around the quadriceps or hamstring, and the lower frame often has straps that wrap around the calf. Each portion of the frame is configured to fit the shape of the corresponding portion of the leg. The hinge allows the lower frame to pivot relative to the upper frame as the knee bends. Many braces have a hinge on each side of the knee joint to give the brace additional strength.

Conventional hinges for knee braces include a single axis pivot, two gears and a four-bar linkage. The conventional geared hinge mechanisms typically have two rotating gears with interlocking teeth. The single axis pivot and geared hinge mechanisms have several disadvantages. First, the single axis pivot and geared hinge mechanisms limit the range of flexion of the leg. Second, the single axis pivot and geared hinges do not simulate the natural movement of the knee joint when the leg bends or extends. The motion of the human knee joint is quite complex and does not rotate uniformly from extension to flexion. Because the single axis pivot and geared hinge mechanisms cannot simulate the natural movement of the knee joint, the knee brace may force the knee into an unnatural position at extension or flexion if the straps on the knee brace are tight. This coupled with forces induced during activity may injure the knee joint. Moreover, a user may loosen the straps to avoid the discomfort resulting from the unnatural movement of the knee joint. If the straps on the knee brace are loose, however, the knee brace will slide down the leg during an activity. Such movement of the knee brace during an activity is uncomfortable and annoying. Additionally, as the knee brace slides down the leg, the straps might not be tight enough to provide the necessary support to the knee.

A four-bar linkage hinge mechanism better simulates the motion of the knee during flexion and extension than geared hinges. Four-bar linkage hinges, however, have several disadvantages. First, the motion of a four-bar linkage hinge is complex, making it difficult to set and adjust stops that limit the range of motion of the knee brace. As a result, patients may not accurately limit the range of motion with four-bar linkage hinge mechanisms. Second, four-bar linkage hinges are bigger than many other types of hinges. A big knee brace hinge can make it more difficult to pull clothes over the brace, and large hinges may interfere with the other knee joint during activities. Therefore, four-bar linkage hinges are not widely used in knee braces.

DETAILED DESCRIPTION

A. Overview

The following disclosure describes several embodiments of bicentric hinges and methods for operating anatomical braces with such hinges. Many specific details of certain embodiments of the invention are set forth in the following description and in FIGS. 1-8D to provide a thorough understanding of such embodiments. One skilled in the art, however, will understand that the invention may have additional embodiments or that the invention may be practiced without several of the details described in the following description. For example, even though many embodiments of the bicentric hinge are described with reference to a knee brace, they can also be used in elbow braces or other braces.

The present invention is directed toward bicentric hinges for use in braces and methods for operating such bicentric hinges. In one embodiment of the invention, a hinge includes a plate, first and second members pivotally coupled to the plate, and a rocker coupled to the plate. The first member is pivotable about a first axis of rotation, and the second member is pivotable about a second axis of rotation spaced apart from the first axis of rotation. The second member is not directly engaged with the first member, and the first member may not be connected to a return mechanism that urges the first member to pivot about the first axis of rotation. The first member has a first recess, and the second member has a second recess. The rocker includes a head at least partially receivable in the first recess and/or the second recess to restrict rotation of one of the first and second members until the other has rotated.

In one aspect of this embodiment, the rocker is pivotally coupled to the plate and pivots between a first position in which the head is received at least partially in the second recess to inhibit rotation of the second member and a second position in which the head is received at least partially in the first recess to inhibit rotation of the first member. In another aspect of this embodiment, the first member includes a tooth that contacts the rocker and pivots the rocker from the first position to the second position when the first member pivots from the first position to the second position.

Another aspect of the invention is directed to methods of operating knee brace hinges. In one embodiment, a method includes pivoting a first member about a first axis of rotation from a first position to a second position, and rotating a second member about a second axis of rotation from a first position to a second position after the first member has substantially reached the second position. The second axis of rotation is spaced away from the first axis of rotation. The first member may not be connected to a return mechanism that urges the first member to pivot about the first axis of rotation. The method further includes returning the first member to the first position and the second member to the first position.

B. Embodiments of Hinges for Use in Braces

Figure 1:
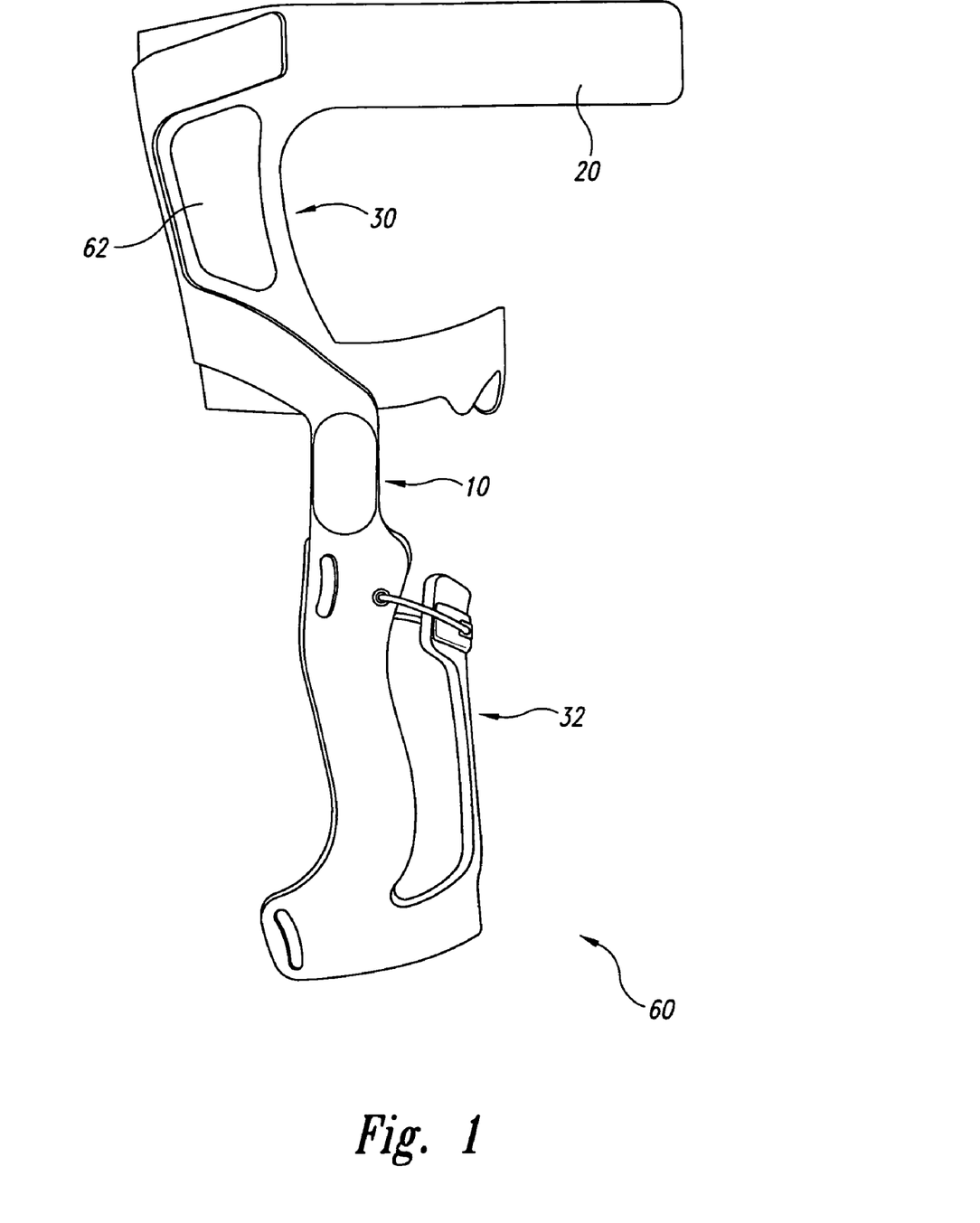
FIG. 1 is an isometric view of a knee brace with a hinge in accordance with one embodiment of the invention.

FIG. 1 is an isometric view of a knee brace 60 including an upper frame 30, a lower frame 32, and hinges 10 connecting the upper frame 30 to the lower frame 32. The upper frame 30 can include at least one strap 20 to wrap around the quadriceps or hamstring, and the lower frame 32 can also include one or more straps. In other embodiments, the upper and lower frames 30 and 32 can have different configurations and include different configurations of straps. For example, the knee brace 60 can also include a flexible, elastic sleeve 62 coupled either directly or indirectly to the upper and lower frames 30 and 32.

Figure 2:
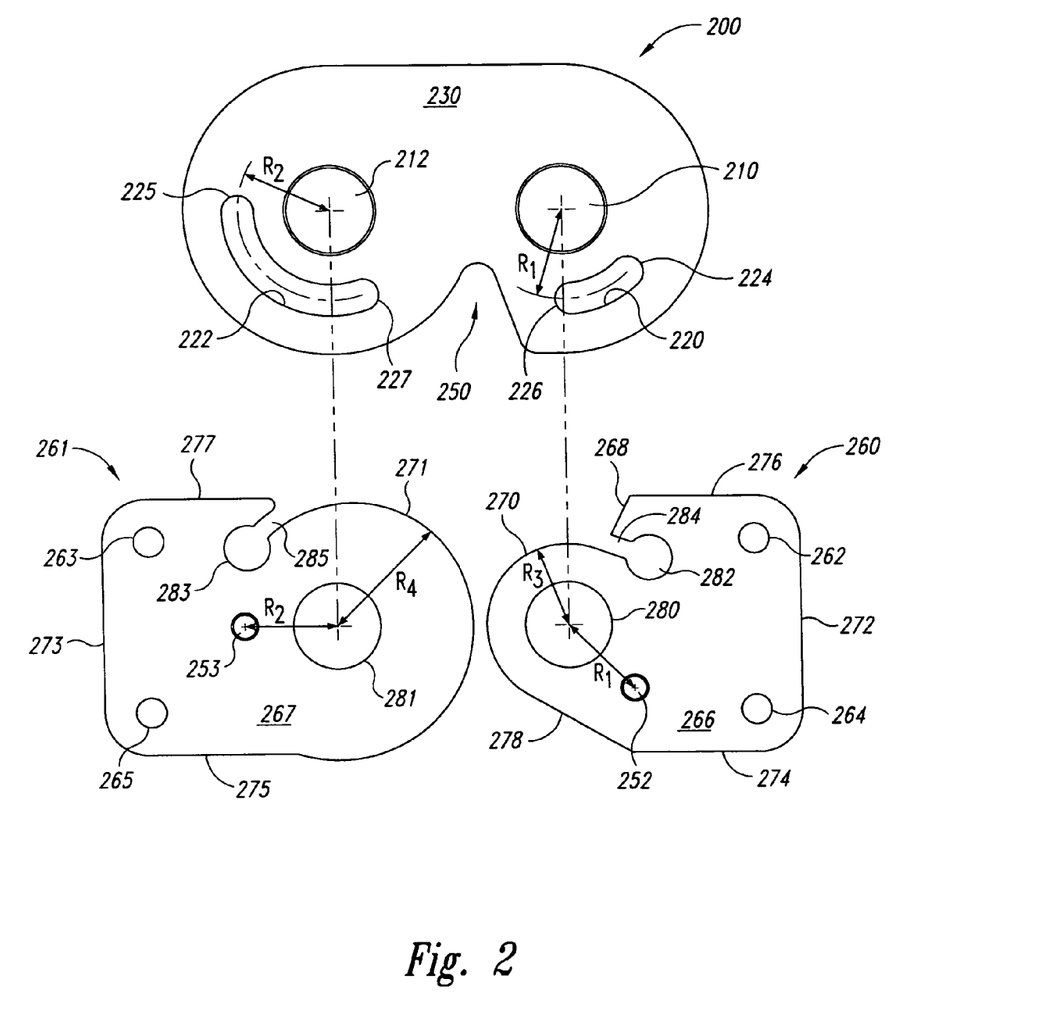
FIG. 2 is an exploded view of a plate, a first hinge member, and a second hinge member of the hinge of FIG. 1.
Figure 3A:
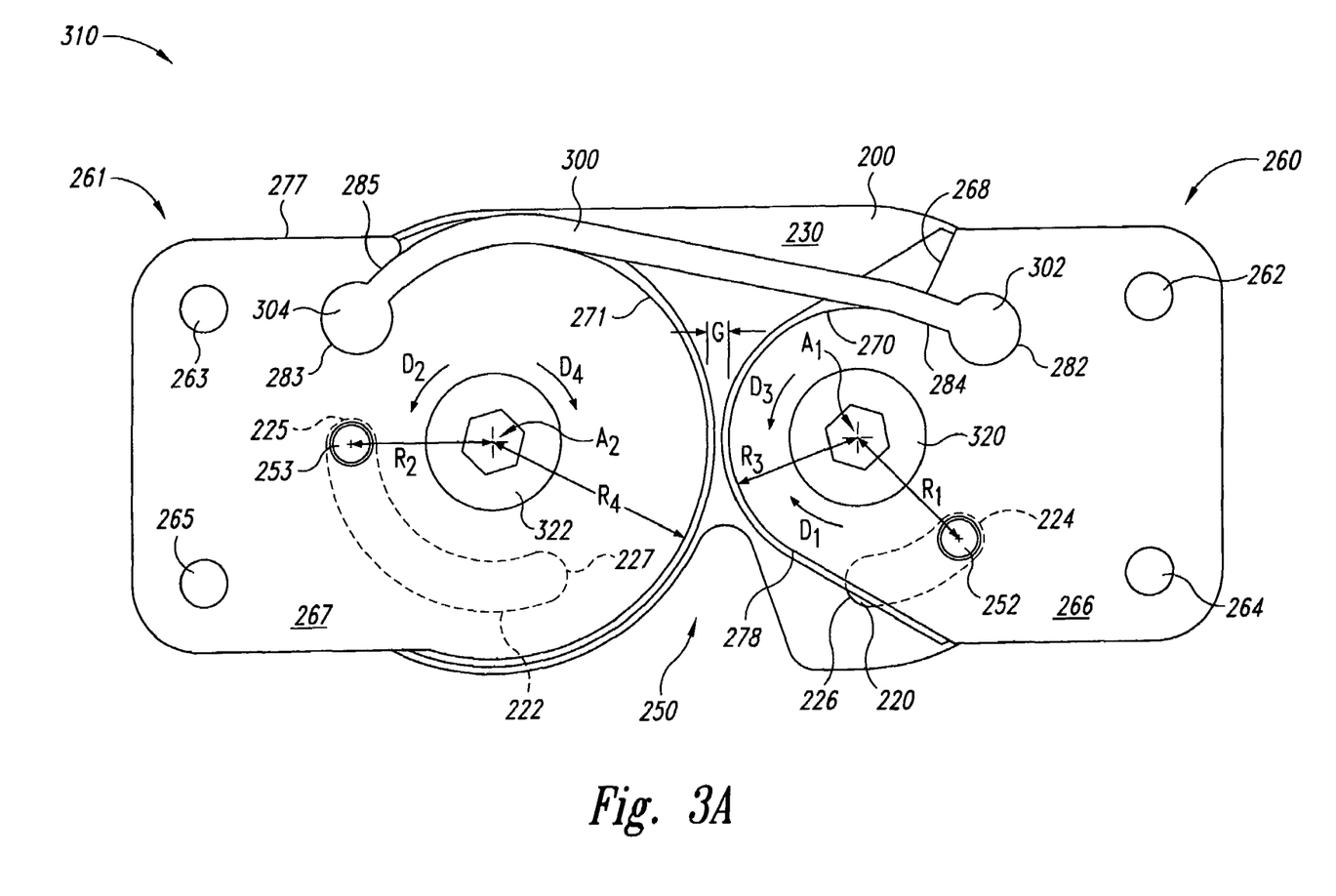
FIG. 3A is a top plan view of an assembly including a resilient member with the plate, the first hinge member, and the second hinge member of FIG. 2.

FIG. 2 is an exploded view and FIG. 3A is a top plan view of one embodiment of the hinge 10. In this embodiment, the hinge 10 includes a back plate 200, a first hinge member 260, and a second hinge member 261. The first hinge member 260 rotatably mounts to the back plate 200 and is configured to attach to the upper frame 30 (FIG. 1) to permit the upper frame 30 to pivot about the back plate 200. The second hinge member 261 also rotatably mounts to the back plate 200 and is configured to attach to the lower frame 32 (FIG. 1) to permit the lower frame 32 to pivot about the back plate 200 independently of the upper frame 30. Accordingly, the upper and lower frames 30 and 32 pivot independently about two different axes of rotation.

Referring to FIG. 2, the first hinge member 260 is a generally flat plate with a front surface 266, a back surface (not shown) opposite the front surface 266, a top edge 276, a bottom edge 274, and a side edge 272. The first hinge member 260 is configured for attachment to a portion of the upper frame 30 and can include two apertures 262 and 264 proximate to the side edge 272 for receiving fasteners (not shown) to connect the upper frame 30 to the first hinge member 260. The second hinge member 261, similarly, has a front surface 267, a back surface (not shown) opposite the front surface 267, a top edge 277, a bottom edge 275, and a side edge 273. The second hinge member 261 is configured for attachment to a portion of the lower frame 32 and can include two apertures 263 and 265 proximate to the side edge 273 for receiving fasteners (not shown) to connect the lower frame 32 to the second hinge member 261. In additional embodiments, the first hinge member 260 can be an integral portion of the upper frame 30 and the second hinge member 261 can be an integral portion of the lower frame 32. The first and second hinge members 260 and 261 can have different configurations in other embodiments.

Referring to FIGS. 2 and 3 together, the first hinge member 260 is pivotally connected to the back plate 200 by a fastener 320 and rotates relative to the back plate 200 about a first axis of rotation $A_1$ (FIG. 3A). The first hinge member 260 has a pin 252 that projects from the front surface 266 and the back surface. The portion of the pin 252 projecting from the back surface is received within an annular slot 220 in the back plate 200. The annular slot 220 is accordingly centered about the first axis of rotation $A_1$ with a centerline at a radius $R_1$ corresponding to the distance from the first axis of rotation $A_1$ to the pin 252. Accordingly, as the first hinge member 260 rotates relative to the back plate 200 about the first axis of rotation $A_1$, the pin 252 slides in the annular slot 220. A first endpoint 224 and a second endpoint 226 of the slot 220 define the maximum range of motion for the first hinge member 260. As such, the length of the slot 220 determines the pivoting range of the first hinge member 260 relative to the back plate 200. In other embodiments, the pin 252 can have a different configuration or shape. For example, the pin 252 can extend or project from either the front surface 266 or the back surface. In additional embodiments, the slot 220 can have different lengths to change the pivoting range of the first hinge member 260. In other embodiments, the position of the slot 220 and the pin 252 can be different, such as the slot 220 can be in the first hinge member 260 and the pin 252 can be attached to the back plate 200.

The second hinge member 261 is pivotally connected to the back plate 200 by a fastener 322 and rotates relative to the back plate 200 about a second axis of rotation $A_2$ (FIG. 3A). The second hinge member 261 has a pin 253 that projects from the front surface 267 and the back surface. The portion of the pin 253 projecting from the back surface is received within an annular slot 222 in the back plate 200. The annular slot 222 is accordingly centered about the second axis of rotation $A_2$ with a centerline at a radius $R_2$ corresponding to the distance from the second axis of rotation $A_2$ to the pin 253. As the second hinge member 261 rotates relative to the back plate 200 about the second axis of rotation $A_2$, the pin 253 slides in the annular slot 222. A first endpoint 225 and a second endpoint 227 of the slot 222 define the maximum range of motion for the second hinge member 261. The length of the slot 222 determines the pivoting range of the second hinge member 261 relative to the back plate 200. In other embodiments, the pin 253 can have a different configuration or shape. For example, the pin 253 can extend or project from either the front surface 267 or the back surface, or there can be two separate pins extending from each surface. In additional embodiments, the slot 222 can have a different length to change the pivoting range of the second hinge member 261. In other embodiments, the position of the slot 222 and the pin 253 can be different, such as the slot 222 can be in the second hinge member 261 and the pin 253 can be attached to the back plate 200.

Referring to FIG. 3A, the curved edge 270 on the first hinge member 260 is spaced away from the curved edge 271 on the second hinge member by a gap G so that the first hinge member 260 and the second hinge member 261 pivot independently about the two different axes of rotation $A_1$ and $A_2$. Because the hinge has two different and independent axes of rotation, it better simulates the natural motion of the knee joint. This is expected to mitigate the sliding of the knee brace down the leg and reduce exerting unnatural forces against the knee joint.

In the illustrated embodiment, the back plate 200 has a cutout portion 250. The cutout portion 250 allows the first and second hinge members 260 and 261 to rotate through the full pivoting range without the upper and lower frames 30 and 32 (FIG. 1) striking the back plate 200.

In the illustrated embodiment, the first hinge member 260 and the second hinge member 261 are operatively coupled by a resilient member 300. The resilient member 300 has a first end 302 attached to the first hinge member 260 and a second end 304 attached to the second hinge member 261. The first end 302 is received within an aperture 282 in the first hinge member 260. A channel 284 connects the aperture 282 to an edge 268 and is sized to receive a portion of the resilient member 300. Similarly, the second end 304 of the resilient member is received within an aperture 283 of the second hinge member 261. A channel 285 connects the aperture 283 to the edge 277 and is sized to receive a portion of the resilient member 300. The first end 302 and the second end 304 of the resilient member 300 are enlarged so that they are not pulled through the smaller channels 284 and 285. In one embodiment, the first end 302 and the second end 304 of the resilient member 300 have a donut shape with a pin in the center. In other embodiments, the first end 302 and second end 304 of the resilient member 300 can be clamped or bonded. In additional embodiments, such as those described below with reference to FIGS. 3B and 8A-8D, the hinge may not include a resilient member.

The resilient member 300 is elastic and provides resistance to the hinge members 260 and 261 during flexion. In one embodiment, urethane can be used; in other embodiments, other materials may be used. The resilient member 300 stretches as the first hinge member 260 rotates in a direction $D_1$ and/or the second hinge member 261 rotates in a direction $D_2$. The resilient member 300 urges the first hinge member 260 to rotate in a direction $D_3$ and the second hinge member 261 to rotate in a direction $D_4$. Accordingly, when no external force is placed on the first and second hinge members 260 and 261, the pins 252 and 253 are drawn toward the first endpoints 224 and 225 of the slots 220 and 222. When an external force is applied to the first hinge member 260 causing rotation in the direction $D_1$, the resilient member 300 stretches elastically and rides along a curved edge 270 of the first hinge member 260. In the illustrated embodiment, the curved edge 270 has a radius $R_3$; however, in other embodiments, the curved edge 270 may not have a constant radius. Similarly, when an external force is applied to the second hinge member 261 causing rotation in the direction $D_2$, the resilient member 300 stretches elastically and rides along a curved edge 271 of the second hinge member 261. In the illustrated embodiment, the curved edge 270 has a radius $R_4$ that is greater than the radius $R_3$. In additional embodiments, the radius $R_3$ can be equal to or greater than the radius $R_4$.

The resilient member 300 and the radii of the hinge members 260 and 261 operate together to control the rotation of the hinge members 260 and 261. For example, when $R_3$ is less than $R_4$, the first hinge member 260 rotates in direction $D_1$ for an arc length before the second hinge member 261 rotates for an arc length in direction $D_2$. This is because greater external force must be applied to rotate a member with a greater radius in light of the counter force applied by the resilient member 300. Accordingly, in the illustrated embodiment, when an external force is applied to the hinge 310, the first hinge member 260 rotates first because its radius $R_3$ is less than the radius $R_4$ of the second hinge member 261. The second hinge member 261 will begin to rotate after the pin 252 of the first hinge member 260 has rotated through at least a portion of its range of motion. The rotation of one hinge member before the rotation of the other hinge member simulates the natural anatomical motion of the knee joint during extension and flexion. A better simulation of the natural motion of the knee joint reduces the movement of the brace down the leg of the user and the tendency of the knee brace to force the knee into unnatural positions.

Figure 3B:
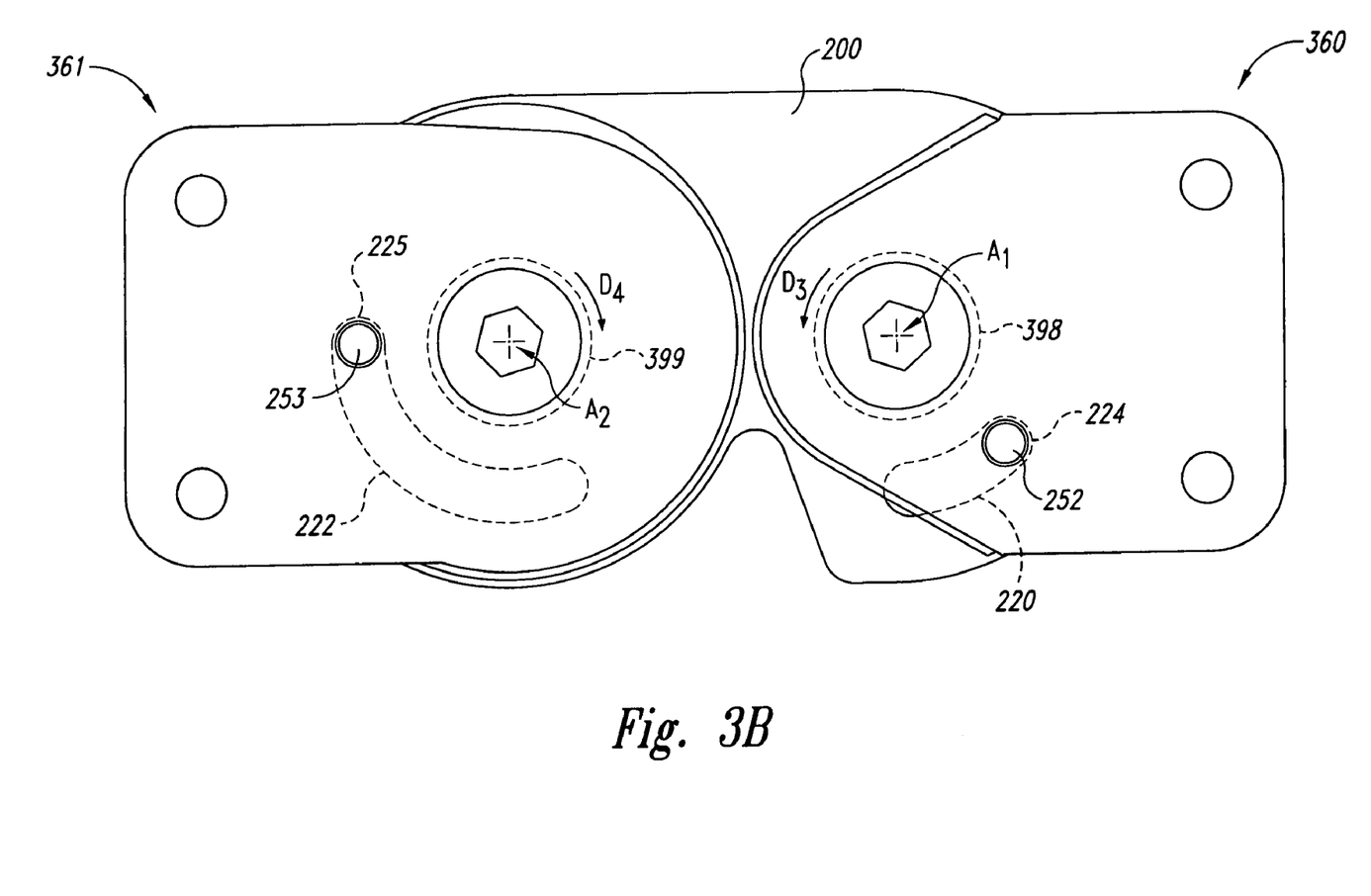
FIG. 3B is a top plan view of an assembly including a first torsion spring attached to a first hinge member and a second torsion spring attached to a second hinge member in accordance with another embodiment of the invention.

FIG. 3B is a top plan view of an assembly including a first torsion spring 398 attached to a first hinge member 360 and a second torsion spring 399 attached to a second hinge member 361 in accordance with another embodiment of the invention. Each torsion spring 398 and 399 is also attached to the back plate 200. The first torsion spring 398 urges the first hinge member 360 to rotate in the direction $D_3$ and the second torsion spring 399 urges the second hinge member to rotate in the direction $D_4$. Accordingly, when no external force is placed on the first and second hinge members 360 and 361, the pins 252 and 253 are drawn toward the first endpoints 224 and 225 of the slots 220 and 222. In one embodiment, the torsion springs can have different spring coefficients causing one hinge member to rotate before the other.

Figure 4:
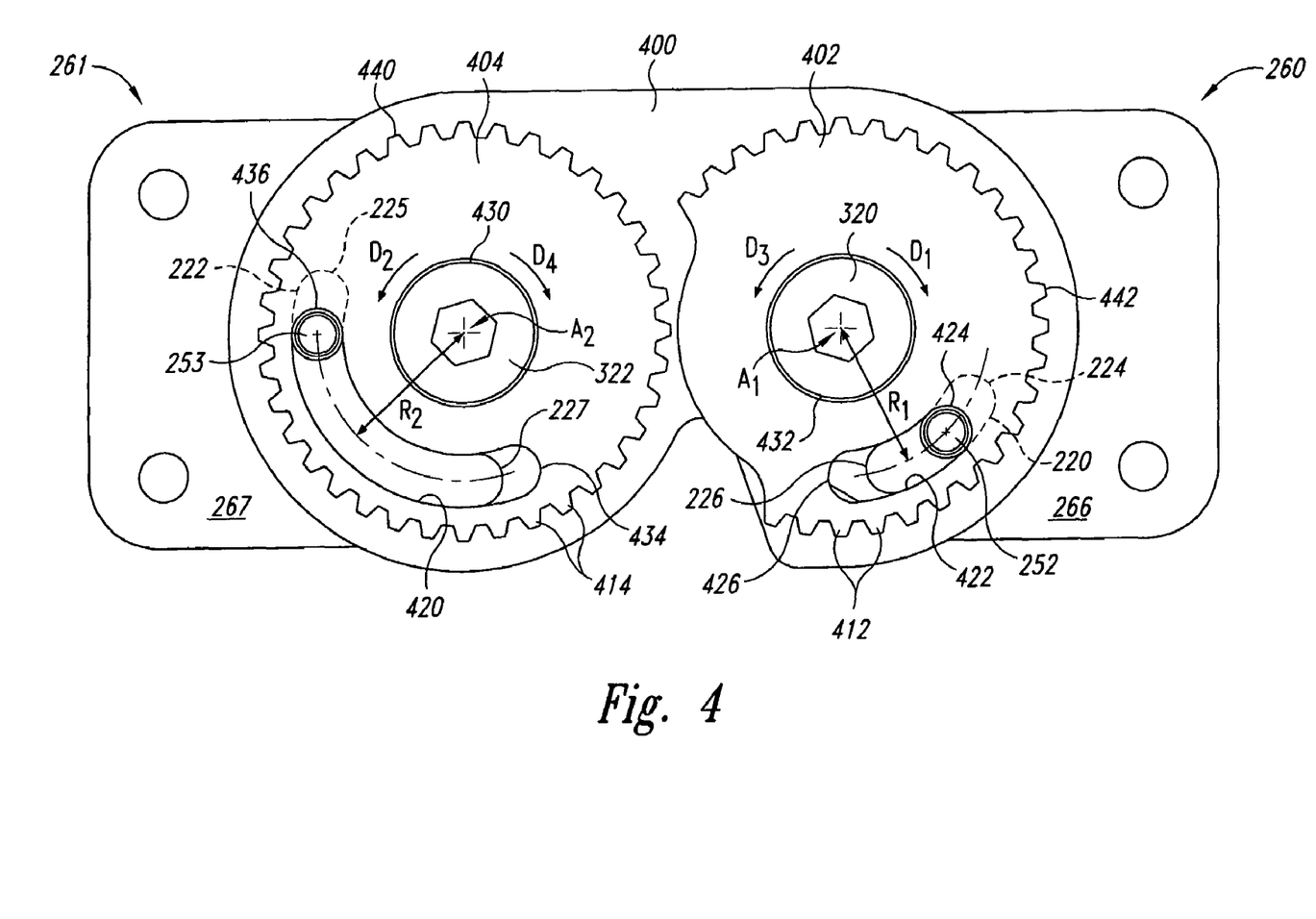
FIG. 4 is a top plan view of first and second adjustable range restrictors.
Figure 5A:
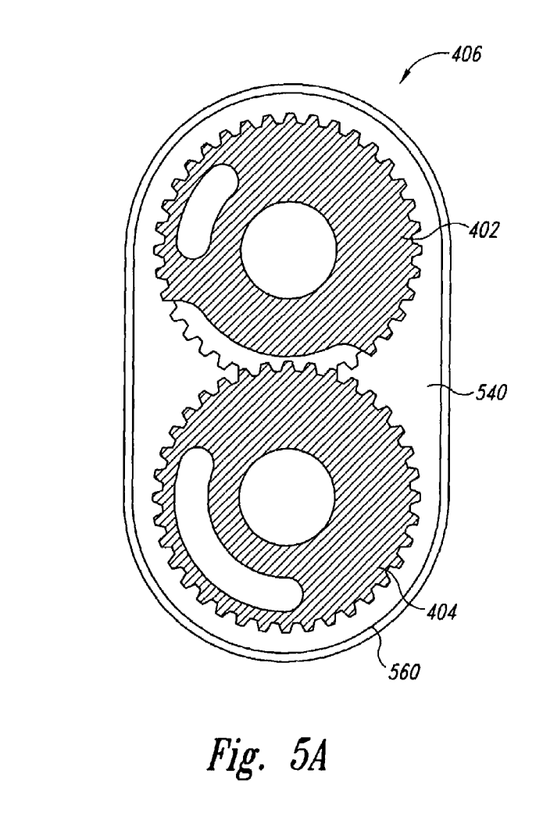
FIG. 5A is a top plan view of an adjustable range restrictor system in accordance with one embodiment of the invention.
Figure 5B:
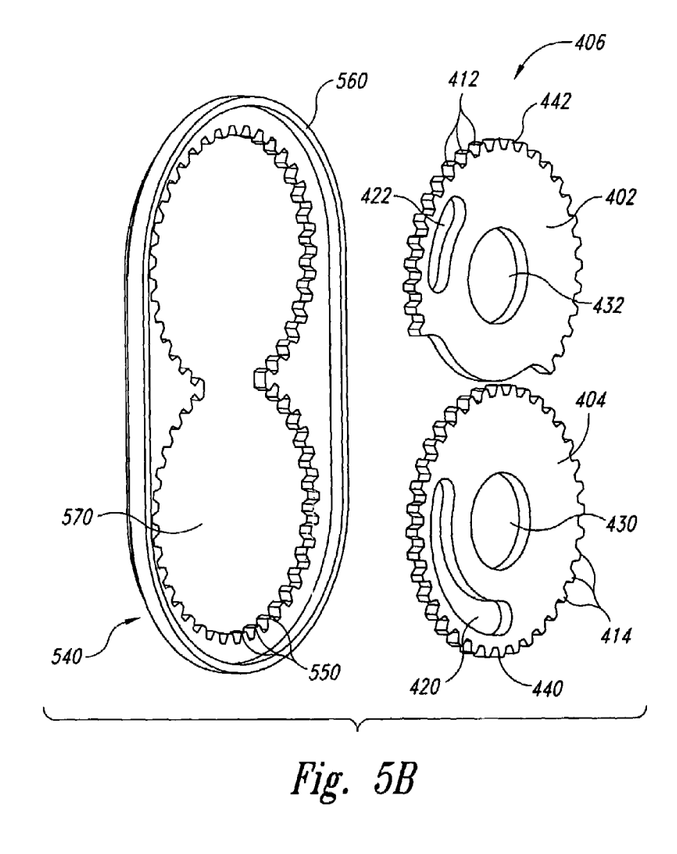
FIG. 5B is an isometric view of the adjustable range restrictor system of FIG. 5A with the first and second adjustable range restrictors removed from a cover plate.

FIG. 4 is a top plan view of the hinge 310 of FIG. 3A with first and second adjustable range restrictors 402 and 404. FIG. 5A is a top plan view of an adjustable range restrictor system 406 in accordance with one embodiment of the invention. FIG. 5B is an isometric view of the adjustable range restrictor system 406 of FIG. 5A with the first and second adjustable range restrictors 402 and 404 removed from a housing 540. As explained in more detail below, the adjustable range restrictor system 406 allows a user to adjust the pivoting range of the first hinge member 260 and/or the second hinge member 261.

Referring to the illustrated embodiment in FIG. 4, the fastener 320 is received in an aperture 432 of the first adjustable range restrictor 402 so that the first adjustable range restrictor 402 is positionable about the first axis of rotation $A_1$. The first adjustable range restrictor 402 has an annular slot 422 extending about the first axis of rotation $A_1$ with a centerline at the radius $R_1$. The slot 422 is positioned and sized to receive the pin 252 of the first hinge member 260. Accordingly, when the first hinge member 260 pivots, the pin 252 moves within the slot 422. Similarly, the fastener 322 is received in an aperture 430 of the second adjustable range restrictor 404 so that the second adjustable range restrictor 404 is positionable about the second axis of rotation $A_2$. The second adjustable range restrictor 404 has an annular slot 420 extending about the second axis of rotation $A_2$ with a centerline at the radius $R_2$. The slot 420 is positioned and sized to receive the pin 253 of the second hinge member 261. Accordingly, when the second hinge member 261 pivots, the pin 253 can move within the slot 420. In the illustrated embodiment, the length of the slot 420 is approximately equal to the length of the slot 222, and the length of the slot 422 is approximately equal to the length of the slot 220. In other embodiments, the slots 420 and 422 can have different lengths.

The first and second adjustable range restrictors 402 and 404 can be rotated so that their slots 422 and 420 limit the rotation of the first and second hinge members 260 and 261. For example, referring to the embodiment in FIG. 4, the first adjustable range restrictor 402 is positioned so that the slot 422 is offset from the slot 220 of the first hinge member 260. Consequently, a first endpoint 424 of the slot 422 and the second endpoint 226 of the slot 220 define stops for the pin 252 to limit the rotation of the first hinge member 260 about the first axis of rotation $A_1$. The first adjustable range restrictor 402 can be rotated further in the direction $D_1$ to further limit the rotation of the first hinge member 260. Conversely, the first adjustable range restrictor 402 can be rotated in the direction $D_3$ to increase the range of rotation. The second adjustable range restrictor 404 can similarly be positioned about the second axis of rotation $A_2$ so that the slot 420 is offset from the slot 222 of the second hinge member 261 to define stops for the pin 253 that limit the rotation of the second hinge member 261 about the second axis of rotation $A_2$.

The adjustable range restrictors 402 and 404 are held in place by the housing 540. Referring to FIGS. 5A and 5B, at least a portion of the outer edge 442 of the first adjustable range restrictor 402 has teeth 412, and the outer edge 440 of the second adjustable range restrictor 404 also has teeth 414. The housing 540 has a recess 570 with teeth 550 that engage the teeth 412 and 414 of the first and second adjustable range restrictors 402 and 404. When the housing 540 is attached to a front plate 400 (FIG. 4), the teeth 550 preclude the first and second adjustable range restrictors 402 and 404 from rotating about the first and second axes of rotation $A_1$ and $A_2$. The housing 540, for example, can have a lip 560 that snap-fits onto the front plate 400 to lock the first and second range restrictors 402 and 404 in desired positions for limiting the range of motion. The first and second adjustable range restrictors 402 and 404 are rotatably adjusted by removing the housing 540, rotating the first and second adjustable range restrictors 402 and 404, and replacing the housing 540. The configuration of the teeth 412, 414 and 550 in the illustrated embodiment permits the first and second adjustable range restrictors 402 and 404 to be adjusted in 10-degree increments. In additional embodiments, the teeth 412, 414 and 550 can be sized and spaced differently.

One advantage of the embodiment of the range restrictor system 406 shown in FIGS. 4-5B is the ease with which a user can adjust the pivoting range of the first and second hinge members 260 and 261. It will be appreciated that the range restrictor system 406 can have other configurations. For example, in additional embodiments, other types of devices can be used to restrict the first and second adjustable range restrictors 402 and 404 from rotating about the first and second axes of rotation $A_1$ and $A_2$. For example, the front plate 400 could have a projection with teeth that engage the teeth of one or both of the adjustable range restrictors 402 and 404, thus eliminating the need for the housing 540. In the illustrated embodiment, the front plate 400 is similar to the back plate 200, but is positioned on the other side of the hinge members 260 and 261. In still other embodiments, the front plate 400 can have a different configuration, or the hinge may not have the front plate 400. In further embodiments, the first and second adjustable range restrictors 402 and 404 can be placed proximate to the first and second hinge members 260 and 261, or the adjustable range restrictor system 406 can be placed adjacent to the back surface of the back plate 200. In additional embodiments, the hinge may not have the adjustable range restrictor system 406.

Figure 6:
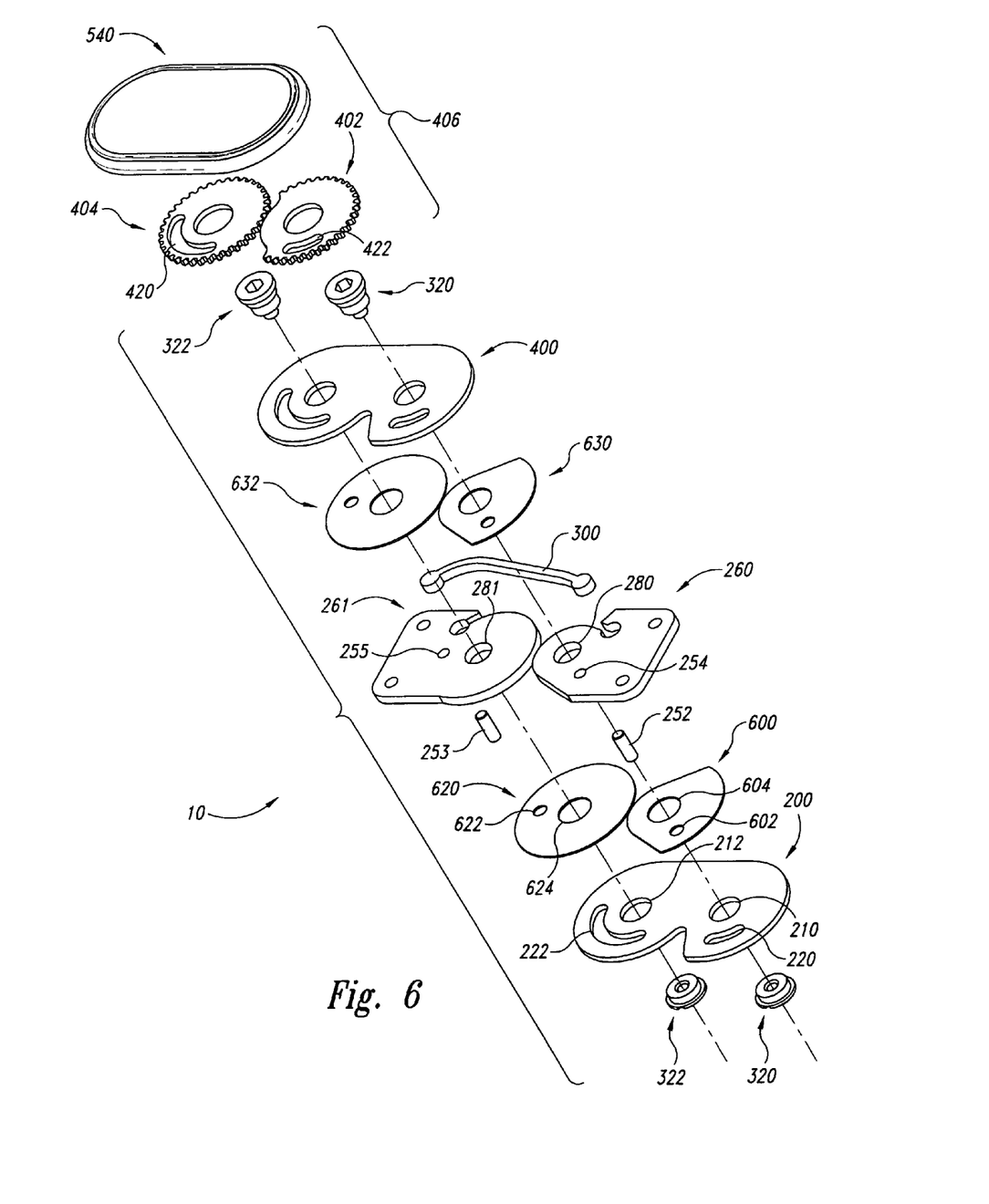
FIG. 6 is an isometric exploded view of a hinge and range restrictor in accordance with an embodiment of the invention.

FIG. 6 is an exploded view of the hinge 10 of FIG. 1. In the illustrated embodiment, the first and second hinge members 260 and 261 are held between the back plate 200 and the front plate 400 by the fasteners 320 and 322. The hinge 10 may have spacers 600, 620, 630 and 632 to assist the first and second hinge members 260 and 261 to rotate more easily between the plates 400 and 200. The spacers 600 and 630 each have an aperture 604 through which the fastener 320 is placed, and an aperture 602 through which the first pin 252 is placed. Similarly, the spacers 620 and 632 each have an aperture 624 through which the fastener 322 is placed, and an aperture 622 through which the second pin 253 is placed. In additional embodiments, the spacers 600, 620, 630 and 632 can have different configurations, or the hinge 10 may not have one or more of the spacers 600, 620, 630 and 632. The range restrictor system 406 attaches to the front plate 400 as explained above.

FIG. 6 also illustrates the compactness of the hinge 10 and the range restrictor system 406. The hinge 10 and the range restrictor system 406 together can have a thickness of between 0.125 inch and 1 inch. In one embodiment, the hinge 10 and the range restrictor system 406 together have a thickness of approximately 0.31 inch. The compact size of the hinge 10 and the range restrictor system 406 makes it easier to wear clothes over the knee brace and reduces the potential of having the hinge interfere with the other knee joint during activities.

C. Additional Embodiments of Hinges for Use in Braces

Figure 7A:
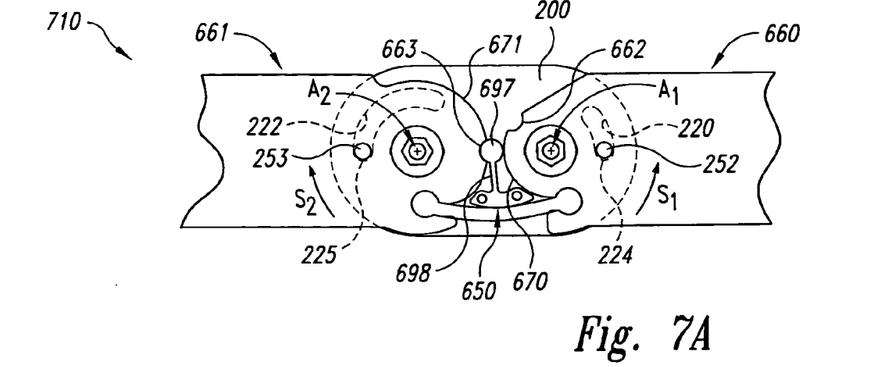
FIGS. 7A-7C are top plan views of a hinge with a rocker in accordance with another embodiment of the invention.
Figure 7B:
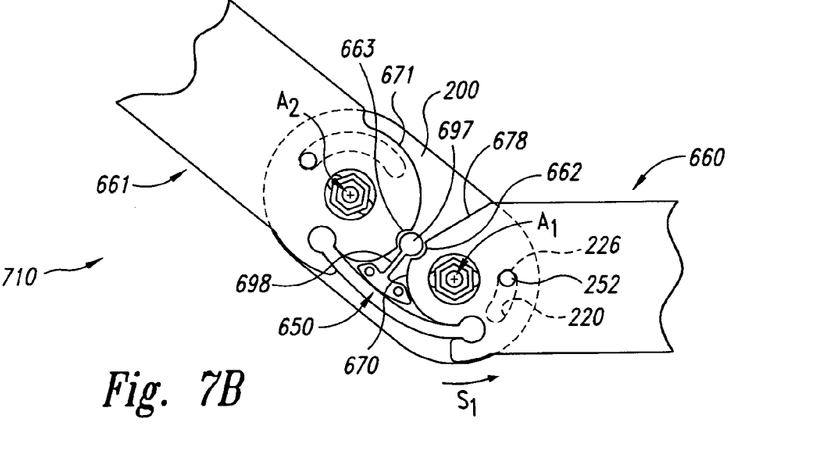
Figure 7C:
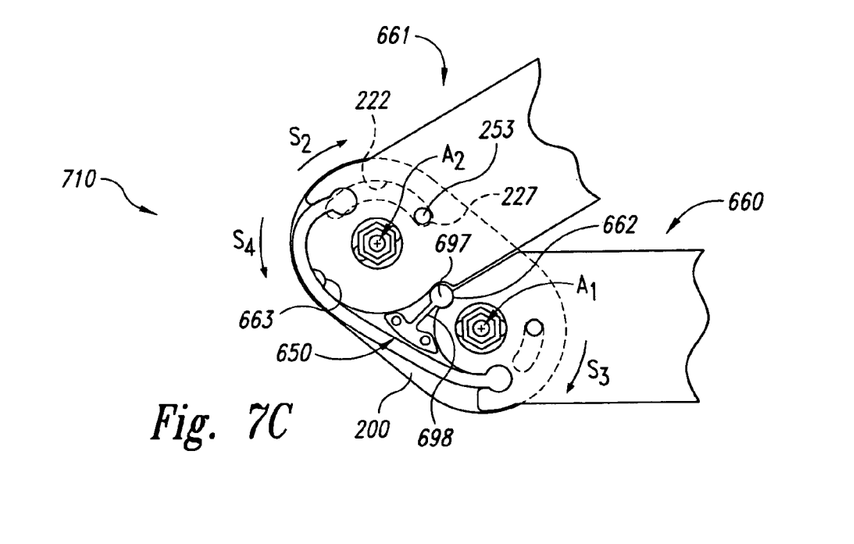

FIGS. 7A-7C are top plan views illustrating a hinge 710 in accordance with another embodiment of the invention. The hinge 710 is similar to the hinge 10 described above, and like reference numbers refer to like components in FIGS. 1-7C. In the illustrated embodiment, the hinge 710 includes a first hinge member 660 with a first recess 662 and a second hinge member 661 with a second recess 663. The first and second hinge members 660 and 661 are pivotally coupled to the back plate 200. Referring to FIG. 7A, the pin 252 of the first hinge member 660 is positioned at the first endpoint 224 of the slot 220 in the back plate 200, and the pin 253 of the second hinge member 661 is positioned at the first endpoint 225 of the slot 222 in the back plate 200. The hinge 710 also includes a rocker 650 attached to the back plate 200. The rocker 650 has a flexible arm 698 and a head 697 positioned between the first hinge member 660 and the second hinge member 661.

When the hinge 710 is in the full-extension position shown in FIG. 7A, the head 697 is proximate to a curved edge 670 of the first hinge member 660 and at least partially within the second recess 663 of the second hinge member 661. Because the head 697 of the rocker 650 is at least partially within the second recess 663 of the second hinge member 661, the second hinge member 661 is effectively jammed and restricted from movement. Accordingly, a force applied to either hinge member 660 or 661 will cause the first hinge member 660 to pivot in a direction $S_1$ about the first axis of rotation $A_1$.

Referring to FIG. 7B, the first hinge member 660 has pivoted about the first axis of rotation $A_1$ to a position where the pin 252 is at the second endpoint 226 of the slot 220 in the back plate 200. The first hinge member 660 accordingly cannot pivot further about the first axis of rotation $A_1$ in the direction $S_1$. In this position, the head 697 of the rocker 650 is received at least partially within the first recess 662 of the first hinge member 660, releasing the bending force on the arm 698. In this position the head 697 is free to move between the two recesses 662 and 663. As the second hinge member 261 begins to rotate about the second axis of rotation $A_2$, the cam shape of the surface 671 forces the head 697 of the rocker 650 into the recess 662 of the first hinge member 660, effectively jamming and precluding rotation of the first hinge member 660 about the first axis of rotation $A_1$.

Referring to FIG. 7C, the second hinge member 661 has pivoted about the second axis of rotation $A_2$ to a position where the pin 253 is at the second endpoint 227 of the slot 222 in the back plate 200. The second hinge member 661 accordingly cannot pivot further about the second axis of rotation $A_2$ in the direction $S_2$. Throughout the rotation of the second hinge member 661 from the position in FIG. 7B to the position in FIG. 7C, the head 697 of the rocker 650 remains in the first recess 662 of the first hinge member 660 precluding the first hinge member 660 from pivoting about the first axis of rotation $A_1$. Because the head 697 of the rocker 650 is at least partially within the first recess 662 of the first hinge member 660, the first hinge member 660 requires a greater force to rotate in a direction $S_3$ than the force required for the second hinge member 661 to rotate in a direction $S_4$. Accordingly, the rocker 650 encourages the second hinge member 661 to pivot in the direction $S_4$ about the second axis of rotation $A_2$ before the first hinge member 660 pivots in the direction $S_3$ about the first axis of rotation $A_1$. In additional embodiments, the hinge 710 can have a rocker with a different configuration, or the hinge may not have a rocker. Furthermore, FIGS. 7A-7C illustrate the full range of extension (FIGS. 7A-B) and flexion (FIGS. 7B-C) of the illustrated embodiment. Other embodiments can also have this range of extension and flexion without the rocker 650 or other components.

FIGS. 8A-8D are top plan views of a hinge 810 in accordance with another embodiment of the invention. The hinge 810 is similar to the hinge 710 described above with reference to FIGS. 7A-7C. For example, the hinge 810 includes a back plate 200, first and second hinge members 860 and 861 rotatably coupled to the back plate 200, and a rocker 880 pivotally coupled to the back plate 200 to selectively inhibit the first or second hinge member 860 or 861 from pivoting, as described in detail below. The illustrated hinge 810, however, does not include a resilient member, a torsion spring, or any other return mechanism to urge the first and second hinge members 860 and 861 to rotate about the first and second axes of rotation $A_1$ and $A_2$, respectively. As such, an external force is required to pivot the first and second hinge members 860 and 861.

Figure 8A:
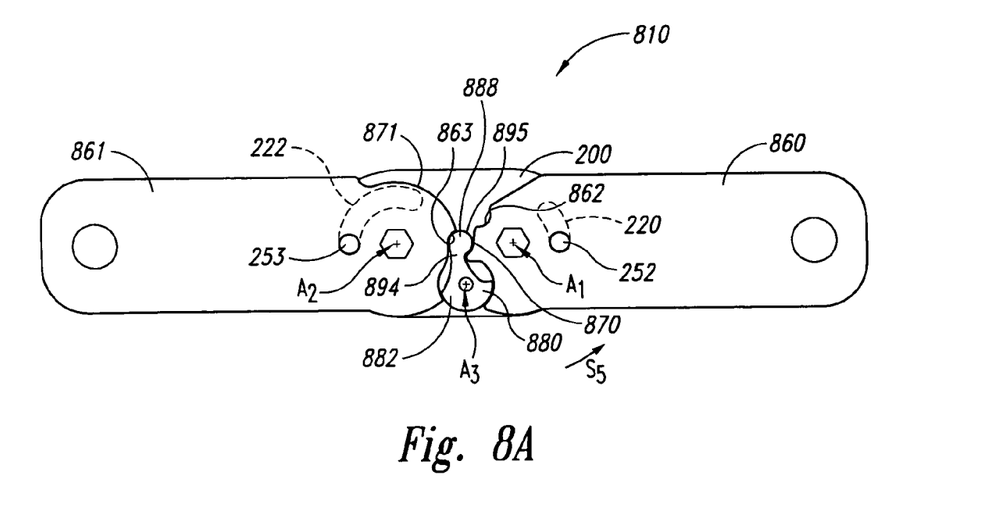
FIGS. 8A-8D are top plan views of a hinge with a rocker in accordance with another embodiment of the invention.

FIG. 8A illustrates the hinge 810 in the full-extension position. The illustrated first hinge member 860 includes a curved surface 870 having a first recess 862, and the illustrated second hinge member 861 includes a curved surface 871 having a second recess 863. The first and second recesses 862 and 863 are sized and shaped to receive a portion of the rocker 880, which when received in one of the recesses 862 or 863, locks the corresponding hinge member 860 or 861 relative to the back plate 200. The first and second hinge members 860 and 861 may also include pins 252 and 253 received in corresponding annular slots 220 and 222 in the back plate 200 to restrict the pivoting range of the members 860 and 861.

The rocker 880 can be a rigid member to inhibit the first or second hinge member 860 or 861 from pivoting until the other member 860 or 861 has rotated. The illustrated rocker 880 includes a base 882 pivotally attached to the back plate 200, a head 888 for engaging the first or second hinge member 860 or 861, and an arm 894 extending between the base 882 and the head 888. The rocker 880 pivots about a third axis of rotation $A_3$ between a first position (shown in FIG. 8A) in which the head 888 is partially received in the second recess 863 to inhibit rotation of the second hinge member 861 and a second position (shown in FIGS. 8C and 8D) in which the head 888 is partially received in the first recess 862 to inhibit rotation of the first hinge member 860. More specifically, when the rocker 880 is in the first position, a round portion 895 of the head 888 is positioned partially within the second recess 863 and against or proximate to the curved surface 870 of the first hinge member 860. Accordingly, a force applied to either hinge member 860 or 861 will cause the first hinge member 860 to pivot in a direction $S_5$ about the first axis of rotation $A_1$.

Figure 8B:
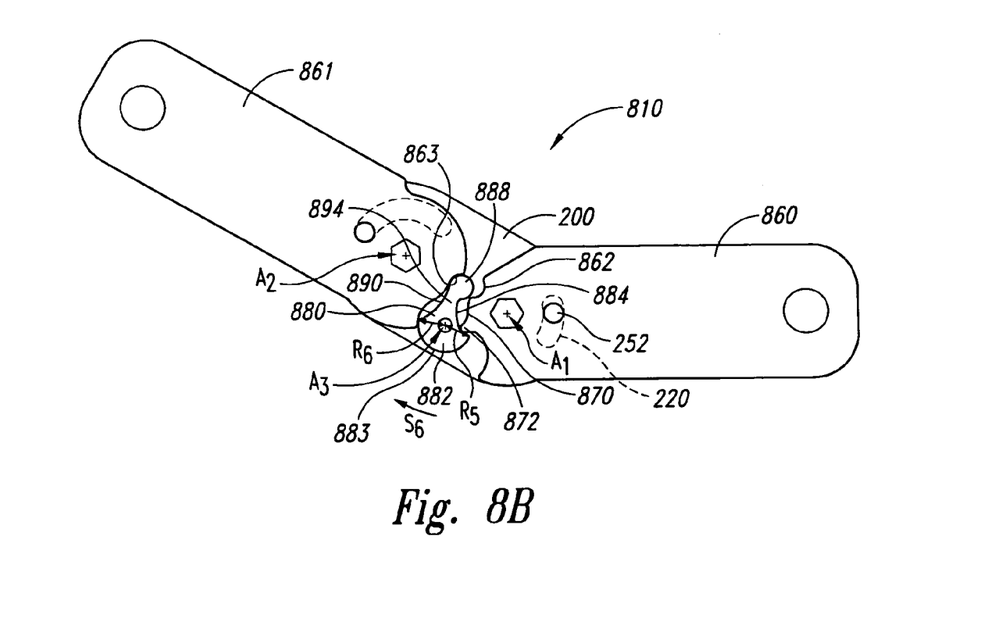

FIG. 8B is a top plan view of the hinge 810 as the first hinge member 860 pivots about the first axis of rotation $A_1$. The illustrated rocker 880 further includes a cammed surface 884 extending from the arm 894 to the base 882, and the first hinge member 860 further includes a tooth 872 projecting from the curved surface 870 that slides over the cammed surface 884 as the first hinge member 860 rotates about the first axis of rotation $A_1$. When the first hinge member 860 approaches the end of its pivoting range, the tooth 872 exerts a force against the cammed surface 884 to cause the rocker to pivot in a direction $S_6$ about the third axis of rotation $A_3$. As the rocker 880 pivots from the first position toward the second position, the head 888 moves out of the second recess 863.

In one aspect of this embodiment, the base 882 of the rocker 880 includes a surface 883 having a first radius $R_5$ proximate to the cammed surface 884 and a second radius $R_6$ proximate to a curved surface 890, which extends from the head 888 to the base 882. The rocker 880 can be attached to the back plate 200 in an eccentric arrangement such that the first radius $R_5$ is greater than or less than the second radius $R_6$. In other embodiments, the rocker 880 may not be eccentric.

Figure 8C:
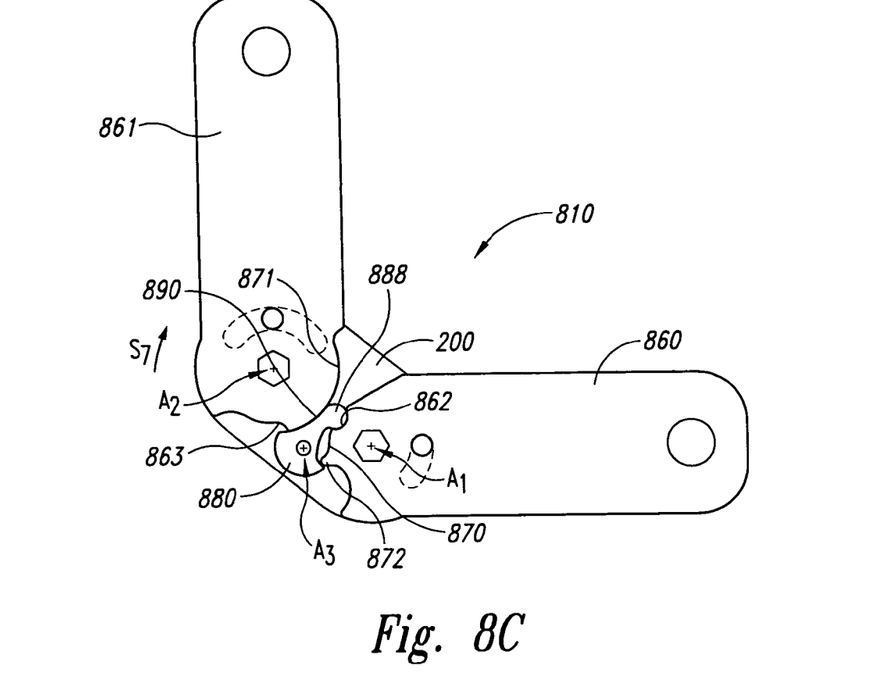

FIG. 8C is a top plan view of the hinge 810 with the second hinge member 861 pivoting in a direction $S_7$ about the second axis of rotation $A_2$. Once the rocker 880 has pivoted from the first position to the second position and the head 888 is partially received in the first recess 862, the first hinge member 860 is inhibited from rotating and the second hinge member 861 is free to rotate about the second axis of rotation $A_2$. Accordingly, the rocker 880 inhibits the second hinge member 861 from pivoting until the first hinge member 860 has reached the end of its pivoting range. The curved surface 871 of the second hinge member 861 and the curved surface 890 of the rocker 880 have complementary configurations such that the second hinge member 861 can slide by the rocker 880 as the member 861 rotates.

Figure 8D:
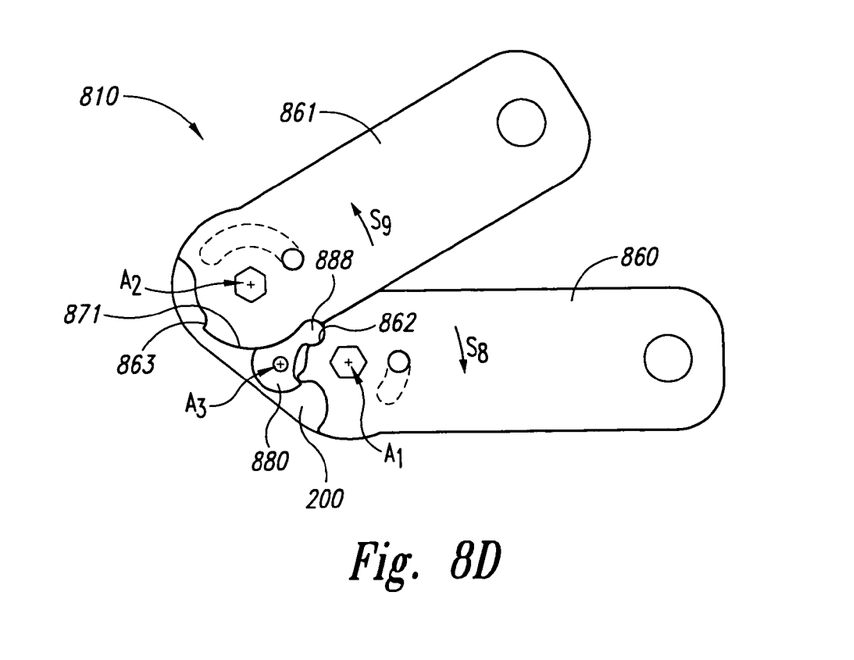

FIG. 8D is a top plan view of the hinge 810 after the second hinge member 861 has reached the end of its pivoting range. Throughout the rotation of the second hinge member 861, the head 888 of the rocker 880 remains in the first recess 862 of the first hinge member 860 and precludes the member 860 from pivoting about the first axis of rotation $A_1$. Because the head 888 is received partially within the first recess 862, the rocker 880 inhibits the first hinge member 860 from rotating in a direction $S_8$ before the second hinge member 861 rotates in a direction $S_9$ back to the position shown in FIG. 8B. In additional embodiments, the hinge 810 can further include the range restrictor system 406 (FIGS. 5A-5B).

One feature of the hinge 810 illustrated in FIGS. 8A-8D is that the rocker 880 inhibits one hinge member from rotating before the other member has rotated. An advantage of this feature is that the rotation of one hinge member before the other simulates the natural anatomical motion of the knee joint during extension and flexion. The improved simulation of the natural motion of the knee joint reduces the movement of the knee brace up and down the leg and the tendency of the brace to force the knee into unnatural positions. Moreover, the illustrated rigid rocker 880 is expected to reduce the play in the hinge 810.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A bicentric hinge for use in a brace, the hinge comprising:
   a plate;
   a first member pivotally coupled to the plate, the first member having a first recess and being pivotable about a first axis of rotation, the first member not being connected to a return mechanism that urges the first member to pivot about the first axis of rotation;
   a second member pivotally coupled to the plate, the second member having a second recess and being pivotable about a second axis of rotation spaced apart from the first axis of rotation, the second member not being directly engaged with the first member; and a rocker coupled to the plate, the rocker having a head at least partially receivable in the first recess and/or the second recess to restrict rotation of one of the first and second members until the other has rotated.

2. The bicentric hinge of claim 1 wherein the rocker is pivotally coupled to the plate and pivots between a first position in which the head is received at least partially in the second recess to inhibit rotation of the second member and a second position in which the head is received at least partially in the first recess to inhibit rotation of the first member.

3. The bicentric hinge of claim 1 wherein the rocker is a rigid member pivotally coupled to the plate.

4. The bicentric hinge of claim 1 wherein:
the first member is pivotable between a first position and a second position;
the first member further includes a tooth; and
when the first member pivots from the first position to the second position, the tooth contacts the rocker and pivots the rocker from a first position in which the head is received in the second recess to a second position in which the head is received in the first recess.

5. The bicentric hinge of claim 1 wherein the second member and the rocker include complementary curved portions.

6. The bicentric hinge of claim 1 wherein:
the first member further includes a first curved portion, and the second member further includes a second curved portion;
the first member pivots between a first position and a second position, and the second member pivots between a first position and a second position;
the head moves across the first curved portion as the first member pivots between the first position and the second position; and
the head moves across the second curved portion as the second member pivots between the first position and the second position.

7. The bicentric hinge of claim 1 wherein the rocker further includes a cammed surface, and wherein the first member further includes a tooth positioned to selectively contact the cammed surface and pivot the rocker from a first position in which the head is received in the second recess to a second position in which the head is received in the first recess.

8. The bicentric hinge of claim 1 wherein the rocker is pivotally coupled to the plate in an eccentric arrangement.

9. A bicentric hinge for use in a brace having a frame, the hinge comprising:
a plate;
a first member rotatably coupled to the plate, the first member being rotatable about a first axis of rotation between a first position and a second position, the first member configured to be attached to the frame;
a second member rotatably coupled to the plate, the second member being rotatable about a second axis of rotation between a first position and a second position, the second axis of rotation being spaced apart from the first axis of rotation, the second member configured to be attached to the frame; and
a rocker coupled to the plate, the rocker being movable between a first position in which the rocker inhibits rotation of the second member and a second position in which the rocker inhibits rotation of the first member;
wherein an external force is required to move the first member between the first and second positions and the second member between the first and second positions.

10. The bicentric hinge of claim 9 wherein:
the rocker is pivotally coupled to the plate and includes a head;
the first member includes a first recess, and the second member includes a second recess;
the head is received at least partially within the second recess when the rocker is in the first position; and
the head is received at least partially within the first recess when the rocker is in the second position.

11. The bicentric hinge of claim 9 wherein:
the first member includes a tooth and a first recess, the second member includes a second recess, and the rocker includes a head;
when the first member pivots from the first position to the second position, the tooth contacts the rocker and pivots the rocker from the first position to the second position.

12. The bicentric hinge of claim 9 wherein the rocker is rigid and pivotally coupled to the plate.

13. The bicentric hinge of claim 9 wherein the rocker includes a cammed surface, and wherein the first member includes a tooth positioned to selectively contact the cammed surface and pivot the rocker from the first position to the second position.

14. A bicentric hinge for use in a brace, the hinge comprising:
a plate;
a first member rotatably coupled to the plate, the first member having a first recess and being rotatable about a first axis of rotation;
a second member rotatably coupled to the plate, the second member having a second recess and being rotatable about a second axis of rotation, the second axis of rotation being spaced apart from the first axis of rotation, the second member not being directly engaged with the first member, and the second member not being connected to a resilient member or a torsion spring that urges the second member to rotate about the second axis of rotation; and
a rocker pivotally coupled to the plate, the rocker having a head and being movable between a first position in which the head is received at least partially within the second recess to inhibit rotation of the second member and a second position in which the head is received at least partially within the first recess to inhibit rotation of the first member.

15. The bicentric hinge of claim 14 wherein:
the first member is pivotable between a first position and a second position;
the first member further includes a tooth; and
when the first member pivots from the first position to the second position, the tooth contacts the rocker and pivots the rocker from the first position to the second position.

16. The bicentric hinge of claim 14 wherein the rocker further includes a cammed surface, and wherein the first member further includes a tooth positioned to selectively contact the cammed surface and pivot the rocker from the first position to the second position.

17. A bicentric hinge for use in a brace, the hinge comprising:
a plate having a first annular slot and a second annular slot;
a first member pivotally coupled to the plate, the first member having a first recess, a tooth, and a first pin projecting into the first annular slot, the first member being pivotable about a first axis of rotation between a first position and a second position;
a second member pivotally coupled to the plate, the second member having a second recess and a second pin projecting into the second annular slot, the second member being pivotable about a second axis of rotation between a first position and a second position, the second axis of rotation being spaced apart from the first axis of rotation; and a rocker pivotally coupled to the plate and having a head, wherein when the first member pivots from the first position to the second position, the tooth contacts the rocker and pivots the rocker from a first position in which the head is received at least partially within the second recess to a second position in which the head is received at least partially within the first recess.

18. The bicentric hinge of claim 17 wherein the rocker further includes a cammed surface, and wherein the tooth selectively contacts the cammed surface to pivot the rocker from the first position to the second position.

19. The bicentric hinge of claim 17 wherein the rocker includes a rigid member.

20. The bicentric hinge of claim 17, further comprising:
a first adjustable range restrictor operatively coupled to the plate, the first adjustable range restrictor having a third annular slot;
a second adjustable range restrictor operatively coupled to the plate, the second adjustable range restrictor having a fourth annular slot; and
wherein the first pin projects into the first and third annular slots, and the second pin projects into the second and fourth annular slots.

21. A bicentric hinge for use in a brace, the hinge comprising:
a plate;
a first member rotatably coupled to the plate, the first member being rotatable about a first axis of rotation;
a second member rotatably coupled to the plate, the second member being rotatable about a second axis of rotation, the second axis of rotation being spaced apart from the first axis of rotation; and
a rocker coupled to the plate, the rocker having a head movable between a first position in which the head inhibits rotation of the second member and a second position in which the head inhibits rotation of the first member.

22. The bicentric hinge of claim 21 wherein:
the first member includes a first recess, and the second member includes a second recess; and
the rocker is pivotally coupled to the plate and pivots between the first position in which the head is received at least partially in the second recess and the second position in which the head is received at least partially in the first recess.

23. The bicentric hinge of claim 21 wherein the rocker is a rigid member pivotally coupled to the plate.

24. The bicentric hinge of claim 21 wherein:
the first member includes a first recess and a tooth, and the second member includes a second recess;
the first member is pivotable between a first position and a second position; and
when the first member pivots from the first position to the second position, the tooth contacts the rocker and pivots the rocker from the first position in which the head is received at least partially in the second recess to the second position in which the head is received at least partially in the first recess.

25. The bicentric hinge of claim 21 wherein:
the first member includes a first recess, and the second member includes a second recess;
the rocker further includes a cammed surface; and
the first member further includes a tooth positioned to selectively contact the cammed surface and pivot the rocker from the first position in which the head is received in the second recess to the second position in which the head is received in the first recess.

26. A knee brace, comprising:
an upper frame; and
a lower frame;
wherein the upper frame is coupled to the lower frame by a bicentric hinge, the hinge including
a plate;
a first member pivotally coupled to the plate, the first member having a first recess and being pivotable about a first axis of rotation, the first member not being connected to a return mechanism that urges the first member to pivot about the first axis of rotation;
a second member pivotally coupled to the plate, the second member having a second recess and being pivotable about a second axis of rotation spaced apart from the first axis of rotation, the second member not being directly engaged with the first member; and
a rocker coupled to the plate, the rocker having a head at least partially receivable in the first recess and/or the second recess to restrict rotation of one of the first and second members until the other has rotated.

27. The knee brace of claim 26 wherein the rocker is pivotally coupled to the plate and pivots between a first position in which the head is received at least partially in the second recess to inhibit rotation of the second member and a second position in which the head is received at least partially in the first recess to inhibit rotation of the first member.

28. The knee brace of claim 26 wherein the rocker is a rigid member pivotally coupled to the plate.

29. The knee brace of claim 26 wherein:
the first member is pivotable between a first position and a second position, and the first member further includes a tooth;
when the first member pivots from the first position to the second position, the tooth contacts the rocker and pivots the rocker from a first position in which the head is received in the second recess to a second position in which the head is received in the first recess.

30. The knee brace of claim 26 wherein the rocker further includes a cammed surface, and wherein the first member further includes a tooth positioned to selectively contact the cammed surface and pivot the rocker from a first position in which the head is at least partially received in the second recess to a second position in which the head is at least partially received in the first recess.

31. A method for operating a knee brace hinge, comprising: pivoting a first member about a first axis of rotation from a first position to a second position, the first member not being connected to a return mechanism that urges the first member to pivot about the first axis of rotation; rotating a second member about a second axis of rotation from a first position to a second position after the first member has substantially reached the second position, the second axis of rotation being spaced away from the first axis of rotation; and returning the first member to the first position and the second member to the first position; and moving a rocker between a first position in which the rocker inhibits rotation of the second member and a second position in which the rocker inhibits rotation of the first member.

32. The method of claim 31, further comprising pivoting the rocker between a first position in which a head of the rocker is received at least partially within a recess in the second member to inhibit rotation of the second member and a second position in which the head is received at least partially within a recess of the first member to inhibit rotation of the first member.

33. The method of claim 31, further comprising pivoting the rocker between a first position in which the rocker inhibits rotation of the second member and a second position in which the rocker inhibits rotation of the first member, wherein pivoting the rocker comprises contacting a cammed surface of the rocker with the first member to move the rocker from the first position to the second position.

34. The method of claim 31, further comprising flexing the rocker between a first position in which the rocker inhibits rotation of the second member and a second position in which the rocker inhibits rotation of the first member.

35. The method of claim 31, further comprising flexing the rocker between a first position in which a head of the rocker is received at least partially within a recess in the second member to inhibit rotation of the second member and a second position in which the head is received at least partially within a recess of the first member to inhibit rotation of the first member.

* * * * *